United States Patent [19]

Nelson et al.

[11] Patent Number: 4,917,688

[45] Date of Patent: Apr. 17, 1990

[54] BANDAGE FOR TRANSDERMAL DELIVERY OF SYSTEMICALLY-ACTIVE DRUG

[75] Inventors: Eric L. Nelson, Newport Beach; Rajaram Vaidyanathan, Laguna Niguel, both of Calif.

[73] Assignee: Nelson Research & Development Co., Irvine, Calif.

[21] Appl. No.: 211,833

[22] Filed: Jun. 27, 1988

Related U.S. Application Data

[63] Continuation of Ser. No. 3,400, Jan. 14, 1987, abandoned.

[51] Int. Cl.⁴ .................. A61F 13/00; A01N 17/00
[52] U.S. Cl. ............................ 604/306; 128/156; 424/447
[58] Field of Search ............. 604/892.1, 896.1, 897.1, 604/289, 290, 303–309; 128/155, 156; 424/443, 447–449

[56] References Cited

U.S. PATENT DOCUMENTS

| | | | |
|---|---|---|---|
| 802,190 | 10/1905 | Heineman | 128/156 |
| 1,602,344 | 10/1926 | Eagle | 604/304 |
| 2,561,071 | 7/1951 | Prisk | 424/449 |
| 2,629,378 | 2/1953 | Barton | 604/307 |
| 2,807,262 | 9/1957 | Lew | 604/307 |
| 3,053,255 | 9/1962 | Meyer | 604/307 |
| 3,212,495 | 10/1965 | Osbourn et al. | 604/307 |
| 3,367,332 | 2/1968 | Groves | 604/290 |
| 3,515,126 | 6/1970 | Fregert | 128/743 |
| 3,598,122 | 8/1971 | Zaffaroni | 424/435 |
| 3,598,123 | 8/1971 | Zaffaroni | 424/435 |
| 3,742,951 | 7/1973 | Zaffaroni | 424/434 |
| 3,797,494 | 3/1974 | Zaffaroni | 424/434 |
| 3,814,095 | 6/1974 | Lubens | 604/307 |
| 3,972,995 | 8/1976 | Tsuk et al. | 424/435 |
| 3,996,934 | 12/1976 | Zaffaroni | 424/434 |
| 4,031,894 | 6/1977 | Urquhart et al. | 424/448 |
| 4,060,084 | 11/1977 | Chandrasekaran | 424/448 |
| 4,160,020 | 7/1979 | Ayer et al. | 424/436 |
| 4,201,211 | 5/1980 | Chandrasekaran et al. | 424/448 |
| 4,230,105 | 10/1980 | Harwood | 128/156 |
| 4,291,015 | 9/1981 | Keith et al. | 424/486 |
| 4,292,301 | 9/1981 | Keith et al. | 424/486 |
| 4,297,995 | 11/1981 | Golub | 128/156 |
| 4,306,551 | 12/1981 | Hymes et al. | 128/156 |
| 4,307,717 | 12/1981 | Hymes et al. | 128/156 |
| 4,321,252 | 3/1982 | Keith et al. | 424/433 |
| 4,336,243 | 6/1982 | Sanwordeker et al. | 424/449 |
| 4,341,208 | 7/1982 | Gordon | 128/156 |
| 4,409,206 | 10/1983 | Stricker | 424/81 |
| 4,423,040 | 12/1983 | Rajadhyaksha | 514/24 |
| 4,438,139 | 3/1984 | Keith et al. | 424/433 |
| 4,460,368 | 7/1984 | Allison et al. | 424/449 |
| 4,460,370 | 7/1984 | Allison et al. | 128/156 |
| 4,470,962 | 9/1984 | Keith et al. | 424/449 |
| 4,486,194 | 12/1984 | Ferrara | 604/308 |
| 4,666,441 | 5/1987 | Andriola et al. | 604/304 |

Primary Examiner—C. Fred Rosenbaum
Assistant Examiner—Sharon Rose
Attorney, Agent, or Firm—Walter A. Hackler; Robert J. Baran

[57] ABSTRACT

A transdermal delivery bandage and system is provided which includes a supply of topically and/or systemically-active drug, an adhesive for releasably securing the bandage to a dermal surface and control means which are separate from the supply of topical and/or systemically-active drug for adjustably controlling surface contact area between the topical and/or systemically-active drug and the dermal surface. The control means are manually operable by a user of the bandage for adjustably controlling the dose of drug to be administered. Alternatively, the maximum available dose from a given bandage may be preselected by a dispensing pharmacist.

28 Claims, 1 Drawing Sheet

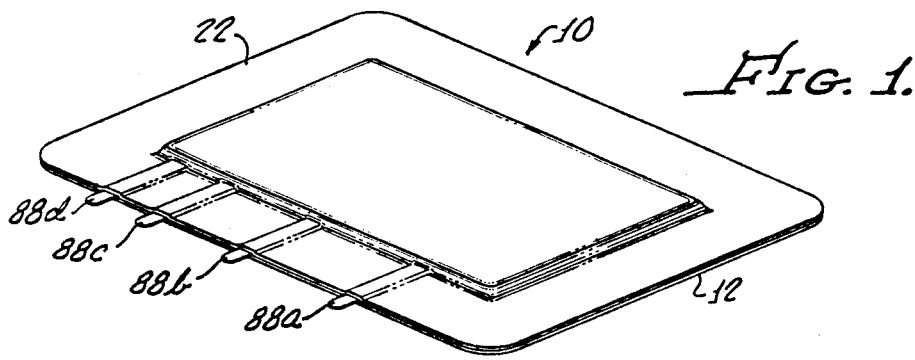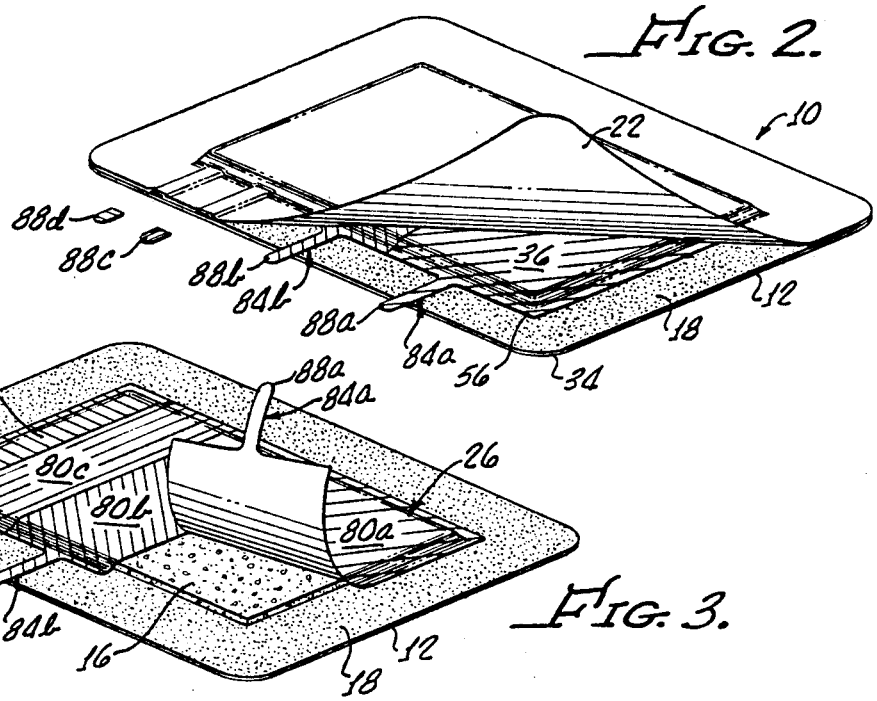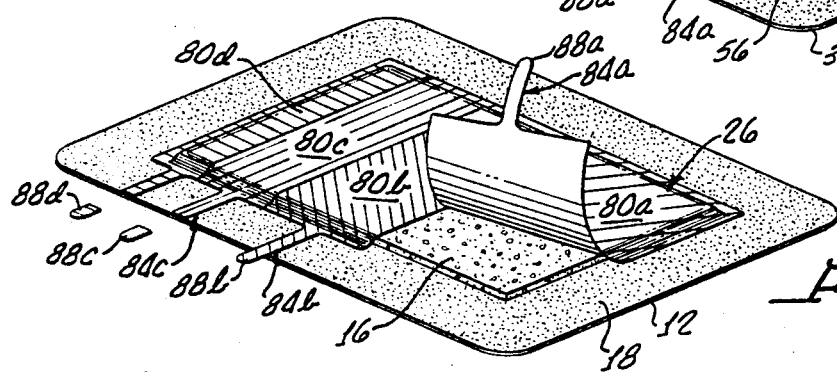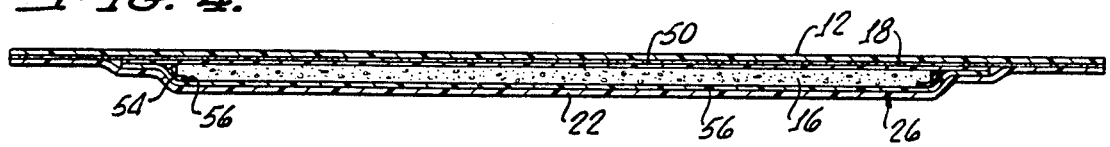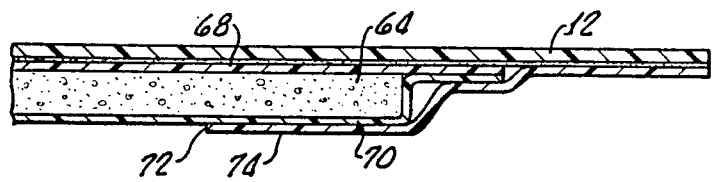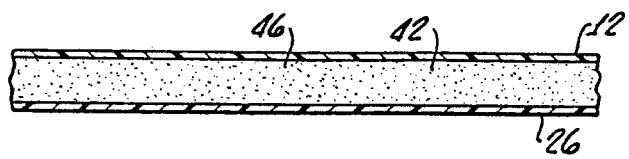

BANDAGE FOR TRANSDERMAL DELIVERY OF SYSTEMICALLY-ACTIVE DRUG

This application is a continuation of application Ser. No. 003,400, filed Jan. 14, 1987 now abandoned.

The present invention is generally directed to a device for the administration of a drug and, more particularly, directed to a medical bandage and system for controlled transdermal delivery of a topical and/or systemically-active drug or agent.

In the treatment of many diseases and/or body conditions, metered, or controlled, medication is most desirable. Unfortunately, intravenous and oral administration of drugs typically results in a non-uniform introduction of the drug into the body's system as a function of time. To overcome this disadvantage, transdermal drug delivery systems have been developed, such as bandages, or the like, which include topically active or systemically-active drugs. In these systems, the drug is absorbed into the body via its dermal surface in a more uniform manner, the drug released by the transdermal system being regulated by both the structure of the system and the area of dermal surface contacted.

Topically active drugs include one or more agents which cause a pharmacological or physiological response at or near the site of the application on a dermal surface. The term "dermal surface", as it is used throughout this specification, is meant to be any skin or mucosa surface.

Systemically-active drugs, on the other hand, include one or more agents which are absorbed through the body via a dermal surface and thereafter distributed throughout the patient's circulatory or lymphatic system to cause a pharmacologic or physiologic response in the patient. A topical and/or systemically-active drug may also include a penetration enhancer if the topical or systemically-active agent does not penetrate the dermal surface in effective quantities. As the name implies, the penetration enhancer acts in concert with the topical or systemically-active agent to facilitate the passage thereof through the dermal surface.

Transdermal systems that have been developed for the delivery of drugs generally may be classified as either a matrix system or a membrane system.

In a matrix system, the drug is suspended in a permeable microporous substrate to form a monolithic body which, when held against a dermal surface by an adhesive, enables diffusion of the drug out of the substrate and into the dermal surface. In this system, the release rate and the amount of drug released is dependent upon the permeability of the microporous structure. In a membrane system, the drug, in a liquid or semi-solid form, is disposed on one side of a membrane which is held to a dermal surface by an adhesive. The membrane functions to regulate, or meter, the drug into the dermal surface.

In each of these systems, the amount of surface area exposed to the dermal surface controls the amount of migration of the drug into the patient's body; that is, each system has a delivery rate over time which is dependent upon the amount of surface contact area between either the monolithic body or the membrane and the dermal surface.

Heretofore, the adhesive in each of these bandage systems has usually been disposed uniformly on the contact surface area so that the drug being administered passes therethrough. While this may be satisfactory with some drugs, those containing a penetration enhancer may also effect an undesired transfer of some component of the adhesive through the dermal surface and into the patient's body.

Each of the transdermal delivery systems hereinabove-described are single dose systems in which the drug dose is determined by the contact area between the drug supporting structure on the dermal surface. Hence, a different size system must be provided for each prescribed drug dose.

Consequently, in order to dispense the bandage system in accordance with a physician's prescribed dose, it is necessary to manufacture and stock an array of bandage systems to supply the needs of patients requiring differing doses of medication. This, of course, gives rise to increased manufacturing, dispensing and storage costs associated with the treatment of any disease or body condition utilizing a transdermal system.

The present invention provides for a bandage for a transdermal delivery of a topical and/or systemically-active drug which enables a pharmacist or end user of the bandage to control the amount of drug being dispensed, thereby adjustably controlling the surface contact area between the topical and/or systemically-active drug and the dermal surface. This feature enables the bandage in accordance with the present invention to provide a varying number of doses of particular drug as may be prescribed by a physician without the necessity for manufacturing an array of bandages having different doses and the concomitant storage and dispensing costs.

SUMMARY OF THE INVENTION

In accordance with the present invention, a bandage for a transdermal delivery of a topical and/or systemically-active agent includes a supply of topical and/or systemically-active agent and adhesive means for releasably securing the bandage to a dermal surface. Control means are provided which are separate from the supply of topical and/or systemically-active agent for adjustably controlling surface contact area between the topical and/or systemically-active agent and the dermal surface when the bandage is held against the dermal surface. By controlling the surface contact area, the control means effectively controls the amount of migration of the topical and/or systemically-active agent into the dermal surface.

More specifically, the control means includes manual means, operable by a user of the bandage for adjustably controlling the surface contact area between the topical and/or systemically-active agent and the dermal surface. The manual means may include at least one selectably removable cover segment disposed over the supply of topical and/or systemically-active agents. Preferably, the manual means includes a plurality of selectably removable cover segments which together form a cover sheet. The cover sheet preferably completely covers the supply of topical and/or systemically-active agent, with the selectably removable cover segments being defined by perforations in the cover sheet. In this manner, the perforations enable manual separation of one or more of the removable cover segments from the cover sheet by tearing along the perforations.

This feature of the present invention enables the user to select a dose to be delivered from any given bandage. Because the dose may be selected at the point of use, storage and dispensing costs can be significantly reduced. Such cost savings result from the elimination of the manufacture of a plurality of bandages, each having a different dispensing dose. As hereinafter summarized in greater detail, selection of the dose may be by the user or by a pharmacist dispensing the bandage.

In accordance with the present invention, the supply of topical and/or systemically-active agent may comprise a microporous material containing a topical and/or systemically-active agent which is permeable to the passage thereof. In this instance, the supply of topical and/or systemically-active agent may be considered a matrix system.

Alternatively, the supply of topical and/or systemically-active agents may comprise a liquid or a gel containing the agent which is separated from the cover sheet by a membrane permeable to the passage of the agent. In this instance, the source of topical and/or systemically-active agent may be considered a membrane-type source.

Preferably, the bandage in accordance with the present invention further comprises a backing sheet with the supply of topical and/or systemically-active agent and adhesive means being disposed on one side of the backing sheet. In instances where the supply of topical and/or systemically-active agents includes a penetration enhancer, it is preferred that the adhesive means is disposed on the backing sheet in a spaced-apart relationship with the supply of topical and/or systemically-active agents. In this manner, the control means can adjustably control, or meter, migration of the topical and/or systemically-active agent into the dermal surface without contact with the adhesive means, thereby eliminating or substantially reducing the possibility of the penetration enhancer causing unwanted migration of components of the adhesive through the dermal surface.

To facilitate use by a patient, the bandage in accordance with the present invention may also include indicia means which are associated with each covered segment for displaying the dosage of topical and/or systemically-active agent delivered into the dermal surface when the bandage is secured in an operational position on the dermal surface with a preselected color segment removed. Preferably, the plurality of selectably removable color segments comprises a set of elongate strips disposed in a parallel relationship with one another over the supply of topical and/or systemically-active agent, with each strip having tab means thereon for manually separating each strip from the cover sheet.

As hereinbefore noted, the bandage in accordance with the present invention may include means for enabling preselective limiting of the operation of the control means to providing a preselected maximum surface contact between the topical and/or systemically-active agent and the dermal surface. In this instance, the tabs on the set of elongate strips are severable, and each tab has a length sufficient to extend beyond a periphery of the bandage to enable preselecting severing thereof.

When the adhesive means of the present invention is disposed along the periphery of the backing sheet and the tab means extend thereover, the adhesive means operates for preventing separation of a tab from the backing sheet and corresponding cover segment from the cover sheet when an end portion means thereon is severed; that is, the adhesive means securely grips the remaining portion of the tab, thereby preventing inadvertent removal of a cover segment. The remaining end portions and tabs are easily gripped in comparison thereto thereby facilitating the removal of cover segments appropriate for the dose described.

As earlier and briefly mentioned, the present invention includes a bandage system for providing multiple doses of a topical and/or systemically-active agent in selectively equal or differing amounts. In this instance, the system comprises a plurality of individual bandage means for transdermal delivery of the topical and/or systemically-active agent, with each of the individual bandage means comprising elements hereinbefore recited.

This system has the advantage of enabling the production of a plurality of bandages, each having a selectable medication dose which eliminates the need for manufacturing, storing and dispensing of an array of bandages having differing doses which otherwise would be necessary.

BRIEF DESCRIPTION OF THE DRAWINGS

The advantages and features of the present invention will appear from the following description considered in conjunction with the accompanying drawings in which:

FIG. 1 is a perspective view showing a bandage in accordance with the present invention having a supply of topical and/or systemically-active agent, adhesive means, control means, as well as a backing sheet and a releasable liner;

FIG. 2 is a perspective view of the bandage shown in FIG. 1 showing the releasable liner partially removed and a plurality of tabs, interconnected with cover segments, with end portions thereof extending beyond a periphery of the bandage;

FIG. 3 is a perspective view of the bandage shown in FIGS. 1 and 2 showing the release liner removed and a cover segment partially removed;

FIG. 4 is a cross-sectional view of the present invention;

FIG. 5 is an enlarged cross-sectional view of the present invention generally showing the supply of topical and/or systemically-active agent incorporating a matrix-type delivery system; and FIG. 6 is an enlarged cross-sectional view of an alternative embodiment of the present invention showing the supply of topical and/or systemically-active agent incorporating a membrane-type delivery system.

DETAILED DESCRIPTION OF THE INVENTION

Turning now to FIGS. 1, 2 and 3, there is shown a bandage, or drug delivery system, 10 in accordance with the present invention which, taken alone, provides for delivery of a topical and/or systemically-active agent, and taken in combination with identical bandages encompasses a system for providing multiple doses of topical and/or systemically-active agent in selectively equal or differing amounts to a dermal surface. (Not shown).

Generally, the bandage 10 includes a backing sheet 12, a supply 16 of topical and/or systemically-active agent, an adhesive 18 disposed on the backing sheet 12, a release sheet 22 and a perforated cover sheet 26 which provides means, separate from the supply 16 of topical and/or systemically-active agent, for adjustably controlling the surface contact area between the supply 16 of topical and/or systemically-active agent and a dermal surface.

It is to be appreciated that it is not necessary to utilize the adhesive 18 for releasably securing the bandage 10 to a dermal surface. For example, a separate elastic band or cloth (not shown) may be utilized to hold the bandage 10 against a person's arm or leg. An adhesive is preferred, however, so that the bandage can be more easily applied to any dermal surface on a person's body.

The backing sheet 12 may be formed of any suitable flexible material, such as mylar or the like. Similarly, the release sheet 22 may be formed of any suitable material and may have a silicone-type coating thereon, not shown, for ensuring adequate release from the adhesive 18, when it is separated therefore to prepare the bandage 10 for application to a dermal surface.

Typical systemically-active agents which may be suitable for use in the present invention are therapeutic agents which are sufficiently potent such that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

The active ingredients of systemically-active agents may include, but are not limited to: Isosorbide Dinitrate, Nitroglycerin, Estradiol, Clonidine, Propranolol, Indomethacine, Nifedipine, Nicardipine, Diclorofenac, Metaproterenol.

Alternatively, a combination of a suitable agent and a penetration enhancer, such as Azone, may be used. When an enhancer is utilized, it is preferred that the adhesive 18 be disposed on the backing sheet 12 along a periphery 34 thereof while the supply 16 is disposed in a center portion 36 thereof to establish a spaced-apart relationship between the adhesive 18 and the supply 16 in order to ensure that the penetration agent does not act to conduct components of the adhesive through the dermal surface, which may be undesirable.

The supply 16 may be of the matrix-type, shown in FIGS. 4 and 5, or membrane-type, shown in FIG. 6. As shown in FIGS. 4 and 5, the supply 16 includes any suitable matrix 42 permeable to the agent disposed in microporous 46 of the matrix. The matrix 42 may be disposed on the backing sheet 12 directly, or on a separate layer 50 attached to the backing sheet by any suitable means. A front sheet 54 may also be provided for supporting the matrix 42 which has an aperture 56 therein to expose the matrix to a dermal surface when the release sheet 22 is removed and the cover sheet 26 partially removed as hereinafter described. The layer 50 and front sheet 54 may be formed from any suitable material, such as mylar or the like.

Alternately, as shown in FIG. 6, the supply of 16 may include a liquid or gel 64 of agent disposed between an impervious layer 68, such as mylar, and a membrane 70, the impervious layer 68 being attached to the backing sheet 12 in any conventional manner. The membrane acts in a conventional manner to limit the migration of the agent therethrough and out an aperture 72 formed in a front sheet 74 when the release sheet 22 is removed and the perforated cover sheet removed, all or in part, as hereinafter described.

Turning now to FIGS. 2 and 3, operation of the bandage is shown in conjunction with the description of the perforated cover sheet 26.

The perforated cover sheet 26 may comprise a set of spaced-apart patterns, each defining cover segments 80a, 80b, 80c, 80d, and it is preferable that the cover segments are formed into elongated strips disposed in a parallel relationship over the supply 16, with each strip 80a, 80b, 80c, 80d, having a tab 84a, 84b, 84c, 84d, thereon, which provides means for manually separating each strip 80a, 80b, 80c, 80d, from the cover sheet 26.

While any number of elongated strips 80a, 80b, 80c, 80d having tabs 84a, 84b, 84c, 84d, interconnected therewith, may be provided, only four are shown in the FIGS. 1, 2 and 3 for the sake of clarity of presentation. Each of the tabs 84a, 84b, 84c, 84d has an end portion 88a, 88b, 88c, 88d, thereon to facilitate manual pulling thereof by the fingers of a user to separate the corresponding tab 84a, 84b, 84c, 84d, from the adhesive 18 and tear the corresponding segment 80a, 80b, 80c, 80d from the perforated cover sheet 26, leaving the remaining elongated strips in place.

A removed strip 80a (FIG. 3) then exposes a preselected contact area which occurs between the supply 16 and a dermal surface (not shown) when the bandage 10 is disposed in an operational relationship with the dermal surface by the adhesive 18. It should be appreciated that the cover segments 80a, 80b, 80c, 80d, may be of varying widths as shown in FIG. 3 to enable a wider selection of doses available from a single bandage 10.

It can be seen from FIGS. 1, 2 and 3 that the tabs 84a, 84b, 84c, 84d, with end portions 88a, 88b, 88c, 88d provide means for enabling preselective limiting of the operation of the control means. Each of the tab means has a sufficient length to allow the end portion 88a, 88b, 88c, 88d to extend beyond the periphery 34 of the backing sheet. Hence, before the release sheet 22 is removed, one or more of the end portions, for example, 88c, 88d, may be clipped flush with the periphery 34 (see FIGS. 2 and 3) to limit the number of end portions 88a, 88b, which may be pulled by a patient. In this manner, the tabs 84c, 84d remaining are secured to the backing sheet 12 by the adhesive 18 thereon and not easily separated therefrom. This limits the dose which the patient may select by pulling the tabs 88a, 88b, and removing the cover segments 80a, 80b. This feature of the invention may have particular importance in the administration of specific drugs in which it is important to ensure that the patient does not inadvertently select a greater dose than that prescribed by the physician.

The severing or cutting of the end portions 80a, 80b, 80c, 80d, may be done on a one-by-one basis, or a jig, not shown, may be provided so that a pharmacist may stack a plurality of the bandages on one another and cut all selected tabs, for example, 80c, 80d, with one operation.

Each of the end portions 88a, 88b, 88c, 88d, as well as the elongated segments 80a, 80b, 80c, 80d, may have various colors (as indicated by different cross hatching in FIG.3) to provide indicia means for displaying the dosage of topical and/or systemically-active agent delivered to the dermal surface when the bandage is secured in operation position on the dermal surface, with preselected cover segments 80a, 80b removed.

It is to be appreciated that any number of bandages and/or systems may be constructed in accordance with the method of the present invention and, although there has been described hereinabove a number of specific bandage embodiments in accordance with the present invention, for the purpose of illustrating the manner in which the invention may be used to advantage, it should be appreciated that the invention is not limited thereto.

Accordingly, any and all modifications, variations or equivalent arrangements which may occur to those skilled in the art, should be considered to be within the scope of the invention as defined in the appended claims.

What is claimed is:

1. A bandage for transdermal delivery of an active agent, said bandage comprising:
a fixed supply of an active agent; a
control means, separate from said fixed supply of active agent, for adjustably and incrementally controlling surface contact area between the fixed supply of active agent and the dermal surface when the bandage is held thereagainst in order to select one of a plurality of available doses greater than zero that can be delivered by the bandage without altering the fixed supply of active agent.

2. The bandage, in accordance with claim 1 wherein said control means includes manual means operable by a user of said bandage for adjustably controlling surface contact area between the fixed supply of active agent and the dermal surface.

3. The bandage in accordance with claim 2 wherein said manual means includes at least two selectably removable cover segments disposed over said supply of active agent.

4. A bandage for transdermal delivery of an active agent, said bandage comprising:
a supply of active agent; and
control means, separate from said supply of active agent, for adjustably controlling surface contact area between the active agent and the dermal surface when the bandage is held thereagainst, said control means including manual means comprising a plurality of selectably removable cover segments, said plurality of selectably removable cover segments together forming a cover sheet, said cover sheet completely covering said supply of active agent, said selectably removable cover segments being defined by perforations in said cover sheet, said perforations enabling manual separation of one or more of the removable cover segments from the cover sheet to control surface contact area between the active agent and the dermal surface.

5. The bandage, in accordance with claim 4 wherein the supply of active agent comprises a microporous material containing said active agent, said microporous material being permeable to the passage of said active agent.

6. The bandage, in accordance with claim 4 wherein the supply of active agent comprises a liquid or gel containing the active agent separated from said cover sheet by a membrane permeable to the passage of the active agent.

7. The bandage, in accordance with claim 4, wherein said perforations define a set of cover segments having differing sizes.

8. The bandage, in accordance with claim 4, wherein said plurality of selectably removable cover segments comprise a set of elongated strips disposed in a parallel relationship over said supply of active agent, each strip having tab means thereon for manually separating each strip from the cover sheet and the fixed supply of active agent.

9. The bandage, in accordance with claim 8, further comprising indicia means, associated within each cover segment, for displaying the dosage of active agent delivered into the dermal surface when the bandage is secured in an operational position on the dermal surface with a preselected cover segment removed.

10. The bandage in accordance with claim 9 wherein the indicia means comprises a plurality of distinguishable colors, each tab means having a different color.

11. A bandage for transdermal delivery of an active agent, said bandage comprising:
a fixed supply of active agent;
adhesive means for releasably securing the bandage to a dermal surface; and
control means, separate from said fixed supply of active agent, for adjustably and incrementally controlling the amount of migration of the active agent into the dermal surface to provide one of a plurality of available doses greater than zero without altering the fixed supply of active agent, said control means including means for controlling surface contact area between the fixed supply of active agent and the dermal surface.

12. The bandage, in accordance with claim 11, further comprising a backing sheet and said fixed supply of active agent and said adhesive means is disposed on one side of said backing sheet.

13. The bandage, in accordance with claim 12, wherein said adhesive means is disposed on said backing sheet in a spaced-apart relationship with said fixed supply of active agent for securing the bandage to a dermal surface in an operational relationship permitting the control means to adjustably control migration of the active agent into the dermal surface without contact with the adhesive means.

14. A bandage for transdermal delivery of an active agent, said bandage comprising:
a fixed supply of active agent;
adhesive means for releasably securing the bandage to a dermal surface;
control means, separate from said fixed supply of active agent, for adjustably controlling surface contact between the fixed supply of active agent and the dermal surface in multiple increments greater than zero; and
means for enabling preselective limiting of the operation of the control means to providing a preselected maximum surface contact between the fixed supply of active agent and the dermal surface.

15. The bandage, in accordance with claim 14, wherein said control means includes means, operable by a user of said bandage, for controlling surface contact area between the fixed supply of active agent.

16. The bandage, in accordance with claim 15, wherein said manual means includes at least two selectably removable cover segments disposed over said fixed supply of active agent.

17. A bandage for transdermal delivery of an active agent, said bandage comprising: manual means comprising a plurality of selectably removable cover segments, said cover segments together forming a cover sheet, said cover sheet completely covering said supply of active agent, said selectably removable cover segments being of the removable cover segments from the cover sheet to control surface contact area between the active agent and the dermal surface.

18. The bandage, in accordance with claim 17 wherein said plurality of selectably removable cover segment comprises a set of elongated strips disposed in a parallel relationship over said supply of active agent.

19. The bandage in accordance with claim 18 when said means for enabling preselective limiting of the operation of the control means comprises a plurality of severable tabs, each one of the plurality of severable tabs being attached to a corresponding cover segment, each said tab having a length sufficient to extend beyond a periphery of the bandage to enable preselective severing thereof.

20. The bandage, in accordance with claim 19, further comprising a backing sheet having the supply of active agent disposed along a central portion thereof and the adhesive means disposed along the periphery of the backing sheet and a releasable protection sheet disposed over said adhesive means.

21. The bandage in accordance with claim 20 wherein each of said severable tabs comprises end portion means, extending beyond the backing sheet, for enabling manual grasping thereof for separating each corresponding tab from the backing sheet and corresponding cover segment from the cover sheet along the perforations therein, said adhesive means including tab adhesive means disposed under each tab, for preventing separation of a severable tab from the backing sheet, and corresponding cover segment from the cover sheet, when the end portion means is removed from the severable tab.

22. A bandage system for providing multiple doses of an active agent in selectively equal or differing amounts, said bandage system comprising: a plurality for individual bandage means of transdermal delivery of the active agent, each said individual bandage means comprising an active agent, adhesive means for releasably securing the individual bandage means to a dermal surface and control means, separate from said supply of active agent, for adjustably and incrementally controlling surface contact area between the active agent and the dermal surface when the individual bandage is secured in an operational position on the dermal surface in order to provide one of a plurality of available doses greater than zero.

23. The bandage system, in accordance with claim 22, wherein said control means of each individual bandage includes manual means operable by a user of said individual bandage for adjustably controlling surface contact area between the active agent and the dermal surface.

24. A bandage system for providing multiple doses of an active agent in selectively equal or different amounts, said bandage system comprising: a plurality of individual bandage means for transdermal delivery of the active agent, each said individual bandage means comprising a supply of the active drug, adhesive means for releasably securing the individual bandage means to a dermal surface and control means, separate from said supply of active agent, for adjustably controlling surface contact between the active agent and the dermal surface when the individual bandage is secured in an operational position on the dermal surface, said control means of each bandage means including manual means, operable by a use of said individual bandage, for adjustably controlling surface contact area between the active agent and the dermal surface, each said manual means including a plurality of selectably removable cover segments disposed over said supply of active agent on each individual bandage means.

25. The bandage system in accordance with claim 24 wherein said plurality of selectably removable cover segments on each individual bandage together forms an associated cover sheet on each individual bandage, each said associated cover sheet completely covering said supply of active agent on each individual bandage, said selectably removable cover segment being defined by perforations in each said associated cover sheet, said perforations enabling manual separation of one or more of the removable cover segments from the associated cover sheet to control surface contact area between the active agent and the dermal surface when each individual bandage is placed in an operational relationship with the dermal surface.

26. The bandage system in accordance with claim 22 further comprising indicia means associated with each cover segment on each individual bandage for displaying the dosage of active agent delivered into the dermal surface when each bandage is secured in an operational position on the dermal surface with a preselected cover segment removed.

27. The bandage systems in accordance with claim 26 wherein the indicia means comprises a plurality of distinguishable colors, each cover segment of each individual bandage having a different color and each cover segment of the same size having the same color.

28. A bandage for transdermal delivery of an active agent, said bandage comprising:
   a supply of an active agent; and
   control means, separate from said supply of active agent for adjustably controlling surface contact area between the active agent and the dermal surface when the bandage is held thereagainst, said control means including manual means comprising selectably removable cover segments, a plurality of said selectably removable cover segments forming a cover sheet, said cover sheet completely covering said supply of active agent.

* * * * *